(12) United States Patent
Hosoi (10) Patent No.: US 7,198,368 B2
(45) Date of Patent: Apr. 3, 2007

(54) OPTOMETRIC APPARATUS

(75) Inventor: Yoshinobu Hosoi, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 568 days.

(21) Appl. No.: 10/624,647

(22) Filed: Jul. 23, 2003

(65) Prior Publication Data

US 2004/0119944 A1 Jun. 24, 2004

(30) Foreign Application Priority Data

Jul. 31, 2002 (JP) ............................. 2002-224278

(51) Int. Cl.
*A61B 3/02* (2006.01)
(52) U.S. Cl. ...................... 351/239; 351/243
(58) Field of Classification Search ........ 351/216–218, 351/233–236, 243, 239; 362/23
See application file for complete search history.

(56) References Cited

U.S. PATENT DOCUMENTS 5,220,362 A * 6/1993 Blenkle ................. 351/235

| | | | |
|---|---|---|---|
| 5,231,430 A | | 7/1993 | Kohayakawa |
| 5,281,984 A | * | 1/1994 | Burton et al. ............. 351/221 |
| 5,485,231 A | | 1/1996 | Hayashi et al. |
| 5,929,971 A | | 7/1999 | Hosoi et al. |

FOREIGN PATENT DOCUMENTS

| JP | U 6-46702 | 6/1994 |
|---|---|---|
| JP | A 7-236612 | 9/1995 |

* cited by examiner

*Primary Examiner*—Hung Xuan Dang
(74) *Attorney, Agent, or Firm*—Oliff & Berridge, PLC (57) ABSTRACT

An optometric apparatus (1) for subjectively examining a visual function of an examinee's eye, includes: a pair of right and left lens chamber units (5), each including a test window (5a) and optical elements to be changeably disposed in the test window; a support unit (6) which supports the lens chamber units so that the units may be converged; a near vision examination chart (2, 3) to be disposed at a changeable distance from the test window; and an illumination unit (7) which illuminates the near vision chart, the illumination unit being provided in each lens chamber unit.

8 Claims, 7 Drawing Sheets

OPTOMETRIC APPARATUS

BACKGROUND OF THE INVENTION

1. Field of the Invention

The present invention relates to an optometric apparatus for a subjective examination of a visual function (a visual acuity, etc.) of an eye of an examinee.

2. Description of Related Art

There has been known an optometric apparatus for subjectively examining a visual function (e.g., a visual acuity, etc.) of an eye of an examinee by switchably disposing optical elements such as spherical lenses and cylindrical lenses in front of the examinee's eye and selectively presenting optotypes before the examinee's eye. Examinations using this type of optometric apparatus include a far vision examination for examining far vision and others by presenting the examination optotypes at a distance of 5 m from the examinee's eye and a near vision examination for examining additional power, near vision, and others by presenting the examination optotypes at a near distance of 15 cm to 70 cm from the examinee's eye.

Figure 7:
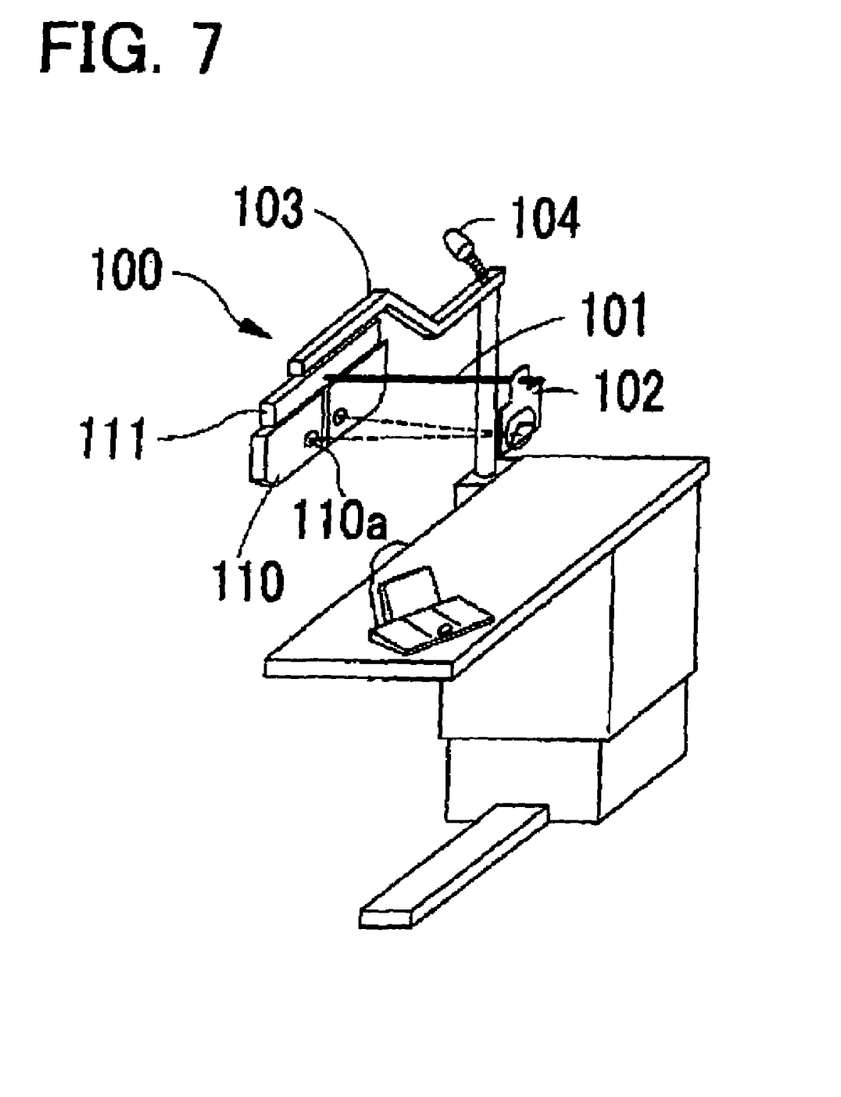
FIG. 7 is a perspective view of an optometric apparatus in a prior art.

In the near vision examination using the above conventional optometric apparatus, for example, an apparatus main unit 100 shown in FIG. 7, a rod 101 is attached to a support unit 111 hanging and supporting a right and left lens chamber units 110 which can be converged, and a chart 102 on which a number of examination optotypes for a near vision examination are drawn is placed at the tip end of the rod 101. An examinee (an examinee's eye) is asked to look at the chart 102 through the optical elements switchably disposed in test windows 110a of the lens chamber units 110. During the examination, the chart 102 is illuminated from above by the light of an illuminator 104, e.g., a fluorescent light or the like, mounted on a support arm 103 which supports the main unit 100.

However, the light of the illuminator 104 illuminating the chart 102 from above may cast the shadow of the rod 101 on the chart 102. Due to such shadow on the chart 102, the examination optotypes would become hard to see. Furthermore, if an inclination angle of the support unit 111 (the lens chamber units 110) with respect to the support arm 103 changes or the position of the chart 102 with respect to the support unit 111 (the lens chamber units 110) changes, it is necessary to adjust the orientation of the illuminator 104.

On the other hand, Japanese utility model unexamined publication No. Hei 6-46702 proposed an optometric apparatus in which an illuminator was mounted near a part at which a rod (bar) supporting a near vision examination chart is fixed, thereby making the illumination direction parallel with an axial or longitudinal direction of the rod. In this case, no shade of the rod is cast on the chart; however, the illuminator being placed near the fixing part of the rod, the chart placed on the same height as test windows of lens chamber units is also illuminated from a position higher than the chart. Consequently, when the chart is moved or slid frontward and backward in the axial direction of the rod to change a presenting distance (position) of the chart, the illumination light axis may not come to almost the center point of the chart. The brightness of the illumination light would therefore change depending on the presenting distance (position).

SUMMARY OF THE INVENTION

The present invention has been made in view of the above circumstances and has an object to overcome the above problems and to provide an optometric apparatus capable of stably illuminating a chart for a near vision examination.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an optometric apparatus for subjectively examining a visual function of an examinee's eye, including: a pair of right and left lens chamber units, each including a test window and optical elements to be changeably disposed in the test window; a support unit which supports the lens chamber units so that the units may be converged; a near vision examination chart to be disposed at a changeable distance from the test window; and an illumination unit which illuminates the near vision chart, the illumination unit being provided in each lens chamber unit.

According to another aspect of the present invention, there is provided an optometric apparatus for subjectively examining a visual function of an examinee's eye, including a pair of right and left lens chamber units, each including a test window and optical elements to be changeably disposed in the test window; a support unit which supports the lens chamber units so that the units may be converged; a support rod provided in the support unit; a near vision examination chart provided movably in an axis direction of the rod; and an illumination unit which illuminates the near vision chart within a movable range of the near vision chart, the illumination unit being provided in each lens chamber unit.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
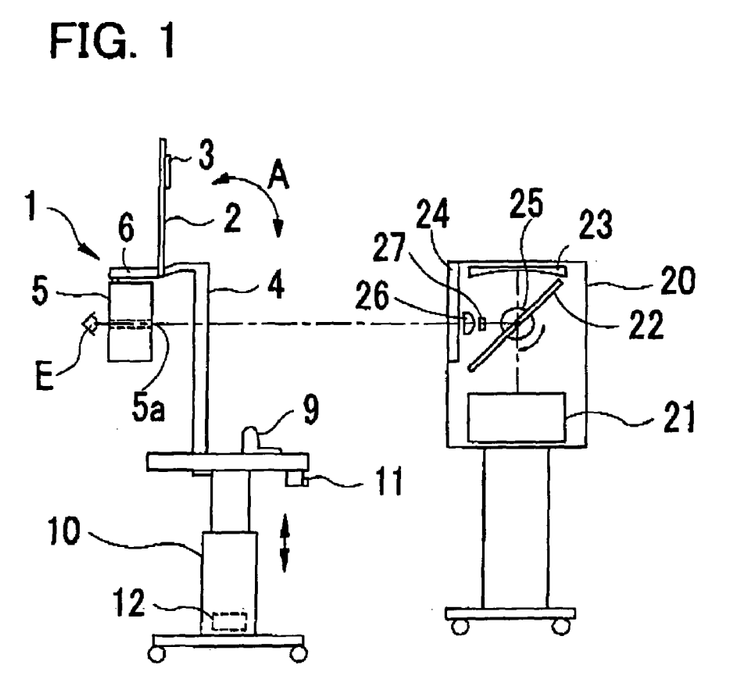
FIG. 1 is a schematic view of an entire optometric system in an embodiment.
Figure 2:
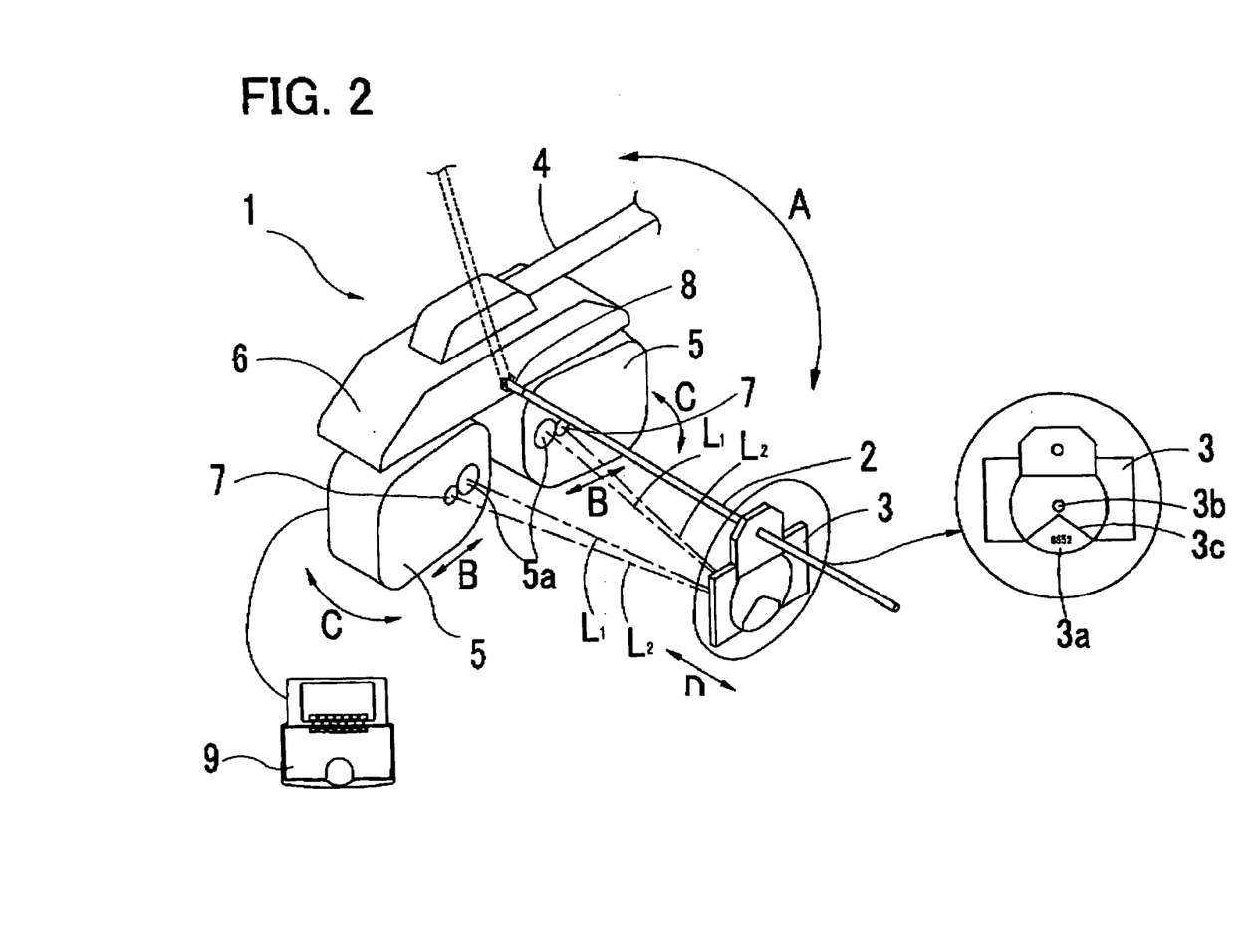
FIG. 2 is a schematic perspective view of an optometric apparatus.

A detailed description of a preferred embodiment of an optometric apparatus embodying the present invention will now be given referring to the accompanying drawings. FIG. 1 is a schematic view of an entire optometric system using the optometric apparatus in the present embodiment. FIG. 2 is a schematic perspective view of the optometric apparatus (in a near vision examination) seen from an examiner side.

Numeral 1 is a main unit of the optometric apparatus, which includes a pair of right and left lens chamber units 5 having symmetric shapes provided with test windows 5a and a support unit 6 which supports (holds) the lens chamber units 5 in a hanging state. The support unit 6 internally houses moving means 40 having a slide mechanism for adjusting the interval between the right and left lens chamber units 5 to change the interval (distance) between the test windows 5a according to the pupillary distance of a patient and a convergence mechanism for adjusting a convergence angle of the lens chamber units 5 (i.e., an angle at which the units 6 are convergently inclined).

Figure 3:
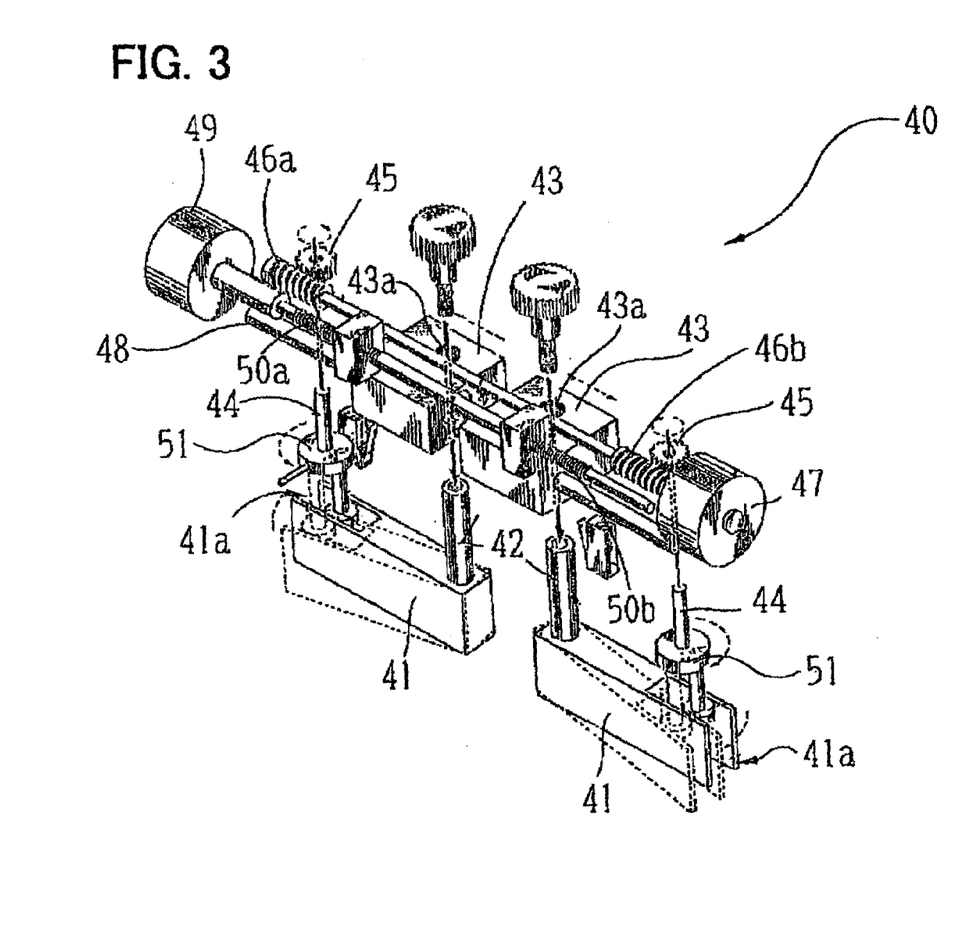
FIG. 3 is a perspective structural view of a slide mechanism and a convergence mechanism of moving means.

FIG. 3 is a perspective structural view showing the slide mechanism and the convergence mechanism of the moving means 40. Shafts 42 fixed to hanging plates 41 which hang the lens chamber units 5 respectively are rotatably engaged in holes 43a of slidable bases 43. Shafts 44 for convergently inclining the hanging plates 41 are connected to worms 46a and 46b respectively through worm wheels 45. The worms 46a and 46b have different threading directions from each other. At each end (lower end in FIG. 3) of the shafts 44, an eccentric shaft 51 is attached. The tip end portion of the eccentric shaft 51 is engaged in a groove 41a formed in the hanging plate 41.

The worms 46a and 46b are connected to a motor 47 and will be rotated by rotation of the motor 47. The rotation of the worms 46a and 46b causes the eccentric shafts 51 to rotate by way of the worm wheels 46 and the shafts 44, thereby converging the hanging plates 41. The slidable bases 43 are movable or slidable on a fixed guide 48 in its axial direction. A motor 49 and the fixed guide 48 are secured to a fixed bracket not shown. To the motor 49, screws 50a and 50b are connected having different threading directions from each other. These screws 50a and 50b are engaged with female screws of the slidable bases 43. When the motor 49 is rotated, accordingly, the two slidable bases 43 are moved or slid in opposite directions. By means of the moving means 40 having the above structure, a distance and a convergence angle between the right and left lens chamber units 5 (the right and left test windows 5a) are adjusted.

The main unit 1 is supported above a table 10 by a support arm 4 provided on the table 10. Numeral 11 is a switch for vertically moving the table 10. This switch 11 is operated to adjust the height of the top plate of the table 10 by means of vertical movement means not shown. Numeral 12 is a relay unit built in the table 10 and is linked to the main unit 1, a controller 9 for drivingly controlling the entire optometric system, an optotype presenting device 20 for presenting optotypes for a far vision examination, and others.

In each lens chamber unit 5, various lens disks are rotatably disposed, on each of which many optical elements (lenses and the like) are mounted in a circumferential arrangement. Each lens disk is rotated by operation of the controller 9 mentioned later to selectively bring one of the optical elements into the test window 5.

Numeral 20 is an optotype presenting device to be used for a far vision examination (FIG. 1 schematically shows the inner structure of this device 20), which is placed at a predetermined distance from the main unit 1. The device 20 is internally provided with optotype presenting means 21 for presenting various kinds of examination optotypes, a half mirror 22, a concave mirror 23, and others. The light of an examination optotype from the presenting means 21 passes through the half mirror 22 and is reflected by the concave mirror 23. The optotype light reflected by the concave mirror 23 is reflected by the half mirror 22 toward an examinee's eye E through a window 24.

The half mirror 22 can change its inclination angle by operation of a motor 25, thereby changing a vertical direction of the optical path of the optotype light. This makes it possible to adjust the optotype light to the height (position) of the eye E. This height (position) of the eye E is detected by a position detecting optical system constructed of a condensing lens 26 and a two-dimensional position detecting element 27 in the optotype presenting device 20. In the present embodiment, two sets of the position detecting optical systems (only one of them being illustrated in FIG. 1) are provided inside the device 20 on the right and the left of the window 24. Infrared light emitted from an illumination part 7 mentioned later in the main unit 1 is received by the position detecting element 27 through the condensing lens 26. Based on an output signal from the position detecting element 27, the height (position) of the eye E can be detected. The details of the method for adjusting the optical path of optotype light to the height (position) of an examinee's eye is referred to Japanese patent unexamined publication No. Hei 7-236612 (U.S. Pat. No. 5,485,231).

Numeral 2 is a rod joined to a joint member 8 provided in the support unit 6. On the rod 2, an optotype presenting unit 3 for use in a near vision examination is mounted movably or slidably in the axial (longitudinal) direction of the rod 2. This unit 3 includes a chart 3a for the near vision examination (hereinafter, referred to as a near vision chart) on which a number of examinations optotypes are drawn or printed. The near vision chart 3a is rotatable about an axis 3b of the presenting unit 3. By rotation of this chart 3a, a desired one of the examination optotypes is presented in a presenting window 3c. The presenting unit 3 is hung on the rod 2 so that the height of the chart 3a to be presented in the presenting window 3c is the same as the height of the test window 5a. The rod 2 is graduated to show a distance from the eye E positioned in front of the test window 5a to the near vision chart 3a. Thus, the chart 3a can be disposed at a desired distance from the eye E during the near vision examination. The joint member 8 is constructed to turn up the rod 2 joined thereto in a direction indicated by an arrow A in FIGS. 1 and 2, so that the rod 2 can be held in a flipped-up position as shown in FIG. 1 (or as indicated by a dotted line in FIG. 2) except when the near vision examination is performed.

Numeral 7 is an illumination part provided in each lens chamber unit 5. The illumination part 7 is used to illuminate the near vision chart 3a (the examination optotype presented in the presenting window 3c) during the near vision examination as shown in FIG. 2. Besides, the illumination part 7 is also used to adjust the presenting position of an examination optotype (the optical path of optotype light) to be presented by the optotype presenting device 20 which is used for a far vision examination. The details thereof will be mentioned later.

This illumination part 7 is provided in the vicinity of each test window 5a in order to prevent the illumination light from casting the shadow of the rod 2 on the chart 3a and to illuminate the chart 3a at any time regardless of the convergence state of the lens chamber units 5. The illumination part 7 is placed so that an optical axis L2 of the illumination light from the illumination part 7 becomes substantially parallel to an examination axis L1 of the test window 5a (including an angle at which the axis L2 comes slightly close to the examination axis L1). The examination axis L1 is a visual line of the eye E looking through the test window 5a.

The illumination part 7 is preferably provided as close as possible to the test window 5a. However, it may be placed anywhere if only the illumination light of a necessary light quantity can be applied to the entire chart 3a without adjusting the direction of the optical axis of the illumination light even when the lens unit chambers 5 are converged according to the presenting distance of the chart 3a (a distance for the near vision examination: about 15 cm to 70 cm). In such case, the placement of the illumination part 7 is also included in the vicinity of the test window 5a.

The illumination part 7 in the present embodiment is placed adjacent to the test window 5a in a horizontal direction, but it is not limited thereto. For instance, the illumination part 7 may be placed adjacent to the test window 5a in a vertical direction or anywhere around the test window 5a.

Figure 4:
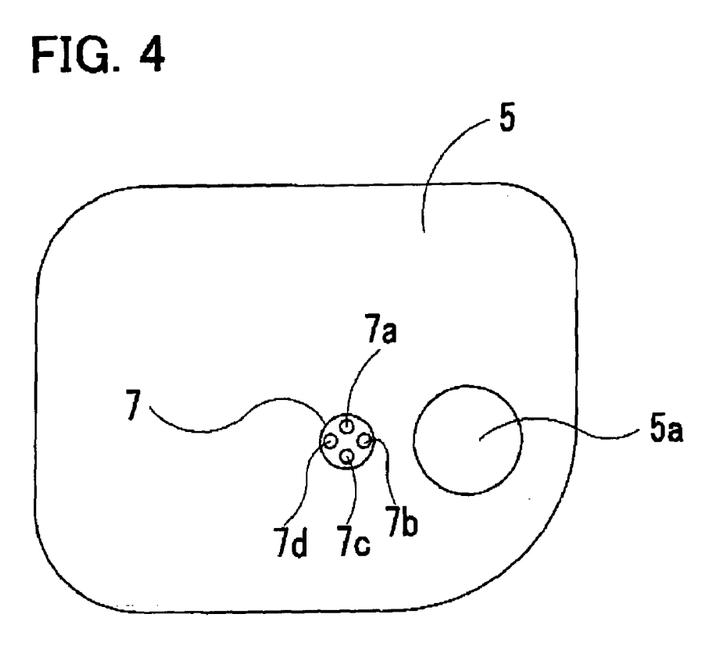
FIG. 4 is a schematic view of a lens chamber unit.

FIG. 4 is a schematic view of one of the lens chamber units 5 to show the details of the illumination part 7. The illumination part 7 is constructed of four LEDs, that is, three white LEDs 7a, 7b, and 7c for illuminating the near vision chart 3a and one infrared LED 7d for emitting infrared light to detect the height of the test window 5a to the optotype presenting device 20. It is to be noted that the white LEDs are used to illuminate the near vision chart 3a in the present embodiment; instead, halogen lamps or the like may be used as illumination sources. However, the white LEDs are preferably used as the illumination sources because they are usable at low voltage and do not practically need lamp replacement.

In the present embodiment, the LEDs 7a–7c for illumination of the near vision chart 3a and the LED 7d for adjustment of the presenting position of the far vision examination optotype are arranged together in the illumination part 7, thus achieving the compact appearance.

In the case where the illumination part 7 is not provided on the same height (in a horizontal direction) as the test window 5a, the inclination angle of the half mirror 22 in the optotype presenting device 20 may be adjusted based on a difference in height between the test window 5a and the position of the LED 7d.

Numeral 9 is a controller for controlling the main unit 1 and the optotype presenting device 20. This controller 9 is provided with switches and others for automatically or manually performing the far vision examination and the near vision examination.

Figure 5:
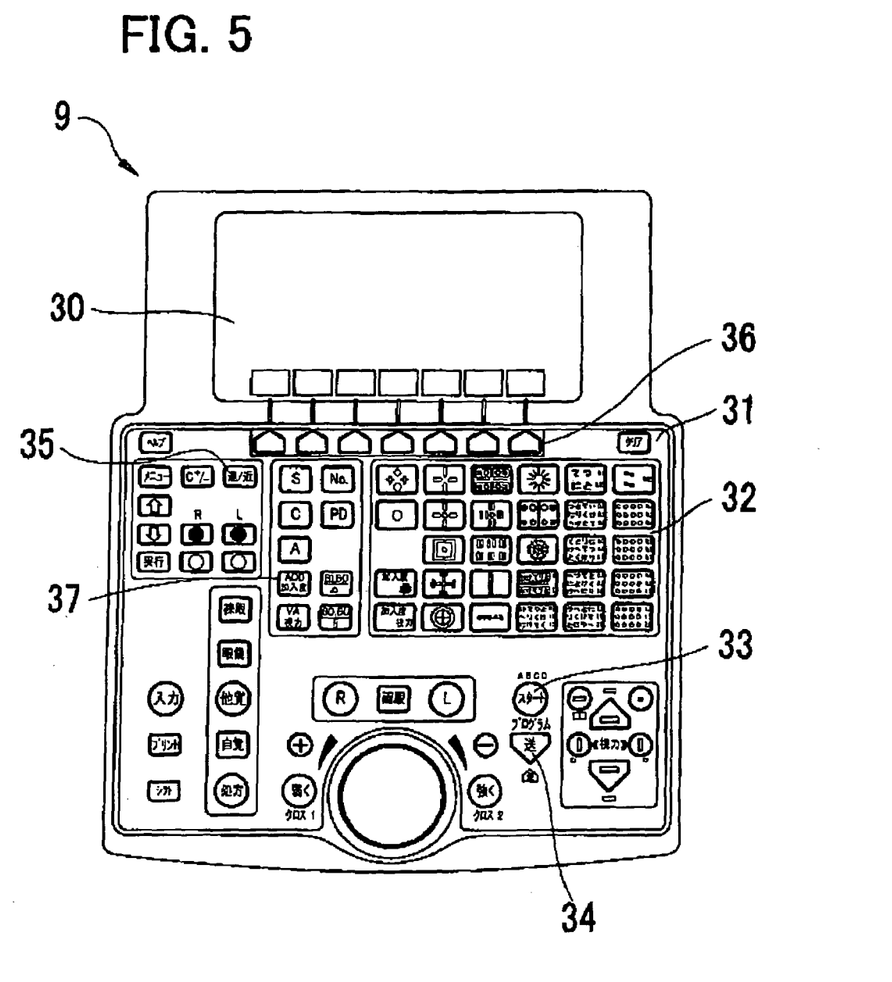
FIG. 5 is a plane view of a controller.

FIG. 5 is a plane view of the controller 9. Numeral 30 is a liquid crystal display for displaying optometry information and others. Numeral 31 is a switch section including a group of optotype switches 32, a start switch 33 for a programmed optometry and an advance switch 34, a far/near switch 35 for switching between a far vision examination mode and a near vision examination mode, a group of function switches 36, and others. The group of function switches 36 are used to select various switch displays displayed at predetermined lower portions in the screen of the display 30 in correspondence with the function switches 36.

Figure 6:
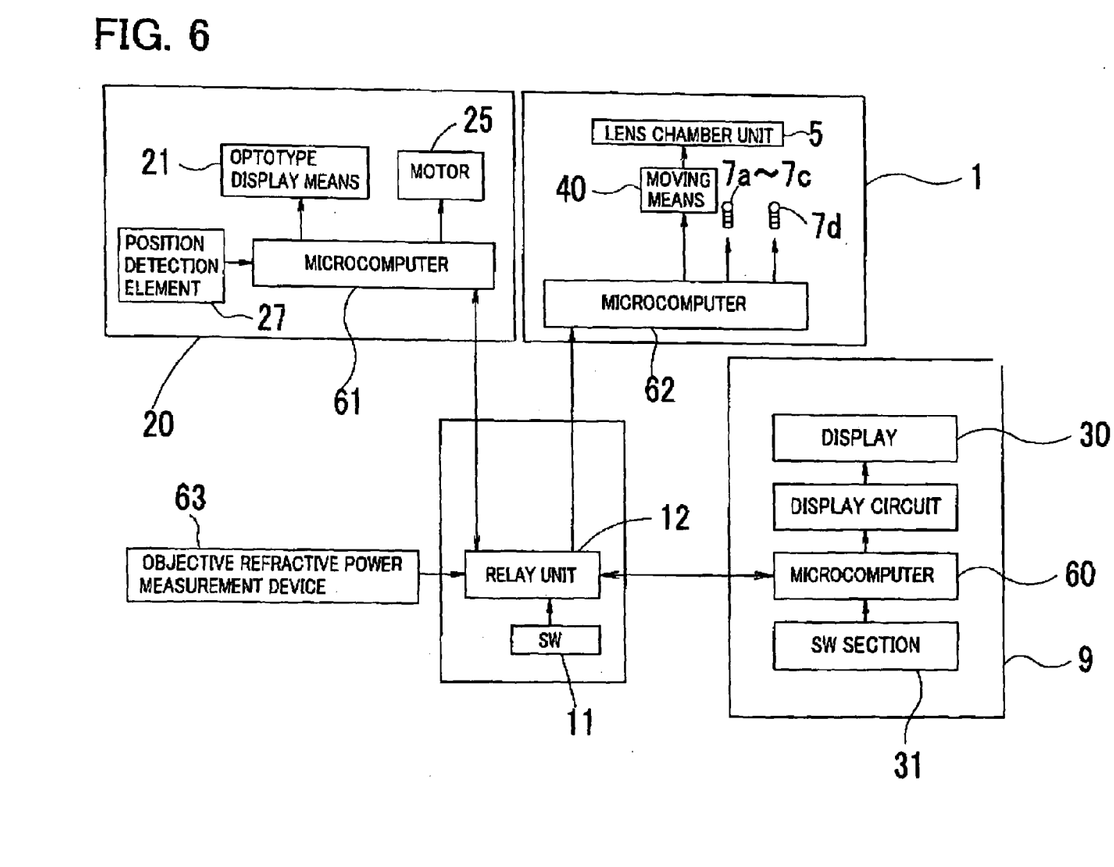
FIG. 6 is a schematic block diagram of a control system.

The operation of the apparatus having the above structure is explained with reference to a schematic block diagram of a control system shown in FIG. 6. Herein, a subjective examination (a far vision examination, a near vision examination) is performed by use of an examination program prepared in advance in relation to a routine of the subjective examination including the near vision examination.

After asking an examinee to sit down in front of the main unit 1, an examiner operates the switch 11 to adjust the height of the main unit 1 to the height of the eye E. While the switch 11 is operated, the output signal is transmitted to a microcomputer 62 of the main unit 1 through the relay unit 12. When the operation of the switch 11 is stopped, interrupting the input signal from the switch 11, the microcomputer 62 causes the LED 7d to emit infrared light to the optotype presenting device 20 for several seconds. The device 20 receives the infrared light from the LED 7d at the position detecting element 27 to detect the height of the eye E, and drives the motor 25 based on the detection data to adjust the inclination angle of the half mirror 22.

The examiner operates the switches in the switch section 31 to input objective examination data (spherical power, astigmatic power (cylindrical power), astigmatic axis, pupillary distance, etc.) determined by an objective refractive power measurement device 68 to the controller 9. The microcomputer 60 transmits the received objective examination data to the main unit 1 and simultaneously causes the display 30 to display the objective examination data. The microcomputer 62 of the main unit 1 controls the moving means 40 to move (slide) the right and left lens chamber units 5 closer to or apart from each other (as indicated by arrows B in FIG. 2) based on the data on the pupillary distance to adjust the interval (distance) between the right and left test windows 5a to the pupillary distance of the examinee. The microcomputer 62 brings the optical element (lens) of a predetermined diopter into one of the test windows 5a and shields the other test window 5a to be unused.

The examiner pushes the switch 33 in the switch section 31 shown in FIG. 5 to start the examination program. The controller 9 transmits a command signal to present an examination optotype to the optotype presenting device 20 in accordance with examination steps of the examination program. Based on the received command signal, the microcomputer 61 of the optotype presenting device 20 controls the optotype presenting means 21 to present the examination optotype.

The examiner pushes an advance switch 34 to advance the examination program to perform adjustment of spherical power, measurements of astigmatic axis and astigmatic power, and others, thereby examining far vision correcting power of the right and left eyes respectively. Thereafter, the examiner pushes the switch 34 to further advance the examination program, which goes into a near vision examination step. At this time, the examination mode of the apparatus is switched from the far vision examination mode to the near vision examination mode. Upon receipt of a signal representing the mode switching to the near vision examination, the microcomputer 62 of the main unit 1 drivingly controls the moving means 40 to converge the right and left lens chamber units 5 (as indicated by arrows C in FIG. 2) by a predetermined amount according to the presenting distance of the near vision chart 3a (i.e., the near vision examination distance). The microcomputer 62 also turns on the LEDs 7a–7c in sync with the switching to the near vision examination mode. It is to be noted that the convergence angle of the lens chamber units 5 is adjusted assuming that the near vision chart 3a is placed at a distance of for example 35 cm from the eye E. The distance for the near vision examination is set in advance by use of the controller 9.

In the near vision examination, the examiner turns down the rod 2 from the flipped-up position into a horizontal position, thereby bringing the near vision chart 3a into front of the test window 5a (the eye E) as shown in FIG. 2. Alternatively, the chart 3a may automatically be placed by a moving device. The examiner moves or slides the near vision chart 3a on the rod 2 in its axial direction (as indicated by an arrow D in FIG. 2) to provide a necessary near vision examination distance. At the start time of the near vision examination, a plurality of near vision examination distances are displayed at a lower portion in the display 30. To adjust the near vision examination distance to 20 cm, 50 cm, or others, a corresponding one is selected from the switches in the group of function switches 36.

Upon selection of the near vision examination distance by the controller 9, the microcomputer 60 transmits the data thereon to the main unit 1. Based on the received data on the near vision examination distance, the microcomputer 62 drives the moving means 40 to adjust the convergence angle of the lens chamber units 5. Thus, in the present embodiment, the lens chamber units 5 in which the illumination parts 7 are provided are converged according to the near vision examination distance even when changed, so that the near vision chart 3*a* can be illuminated without adjustment of the optical axis of the illumination light. Furthermore, the placement of the illumination part 7 in the vicinity of the test window 5*a* also enables even the periphery of the examination optotypes on the chart 3*a* to be illuminated at any time.

Even where a mechanism capable of moving or sliding the presenting unit 3 in a crosswise direction with respect to the rod 2 is added and an examination of the accommodation power of a single eye for near vision is performed on only one eye of an examinee, the optometric apparatus in the present embodiment can illuminate the near vision chart 3*a* without needing adjustment of the illuminating direction because the illumination part 7 is placed in the vicinity of each test window 5*a*.

The examiner conducts the near vision examination on each of the right and left eyes of the examinee to make a check on spherical power, and others. After completion of the near vision examination, the examiner pushes a print switch on the controller 9 to print out the examination data. In response to the print switch signal, the examination program is also terminated, the examination mode is switched from the near vision examination mode to the far vision examination mode, and the microcomputer 62 turns off the LEDs 7*a*–7*c* of the illumination part 7.

In the above mentioned embodiment, the examination program to sequentially execute the far vision examination and the near vision examination is explained, but it is not limited thereto. The present invention may be applied to the case where only the near vision examination is performed. If only the near vision examination is performed in the present embodiment, the switch 35 is pushed to switch the examination mode from the far vision examination mode to the near vision examination mode. Based on this mode switching signal, the convergence angle of the lens chamber units 5 is adjusted to the near vision examination distance previously determined and the LED 7*a* to 7*c* are turned on.

When the examination mode is switched again from the near vision examination mode to the far vision examination mode, the LEDs 7*a*–7*d* are turned off. Furthermore, in another examination mode to change additional power with respect to the far vision by use of a switch 37, similarly, the near vision chart 3*a* is used and the convergence angle of the lens chamber units 5 is controlled. This mode is thus regarded as being included in the near vision examination mode.

In the above embodiment, the illumination sources are turned on in sync with the near vision examination mode switching signal. Instead, a switch may additionally be provided in the joint member 8 so that the LEDs 7*a*–7*c* are turned on when the rod 2 is turned down into the horizontal position (and the LEDs 7*a*–7*c* are turned off when the rod 2 is turned up into the flipped-up position). As a matter of course, the controller 9 may be provided with a switch for arbitrarily turning on/off the LEDs 7*a*–7*c*.

In the above embodiment, the quantity of illumination light of the illumination part 7 is not changed according to the presenting distance (the near vision examination dis-tance) of the near vision chart 3*a* in the near vision examination. Alternatively, it may be changed based on detection or acquisition of the presenting distance (position) of the near vision chart 3*a*, for example, in the following manner. The illumination light quantity of the illumination part 7 is determined in advance according to the near vision examination distance. When a corresponding near vision examination distance is selected by use of one of the function switches 36 on the controller 9 during the near vision examination, the microcomputer 62 obtains the data on the selected near vision examination distance. Based on the data, the microcomputer 62 controls the illumination part 7 to emit light of the illumination light quantity corresponding to the selected near vision examination distance. Such control can achieve more stable illumination of examination optotypes regardless of the presenting distance of the near vision chart (namely, the near vision examination distance).

As described above, according to the present invention, the near vision chart can be illuminated stably.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An optometric apparatus for subjectively examining a visual function of an examinee's eye, including:
    a pair of right and left lens chamber units, each including a test window and optical elements to be changeably disposed in the test window;
    a support unit which supports the lens chamber units so that the units may be converged;
    a near vision examination chart to be disposed in front of the test window at a changeable distance from the test window; and
    an illumination unit which irradiates illumination light to the near vision examination chart, the illumination unit being provided in each lens chamber unit.

2. The optometric apparatus according to claim 1, wherein the illumination unit is provided near the test window of the lens chamber unit so that an illumination optical axis is almost parallel to an examination axis of the test window.

3. The optometric apparatus according to claim 1, wherein the illumination unit is provided with a white LED as an illumination light source.

4. The optometric apparatus according to claim 1, wherein the illumination unit is provided with a white light source and an infrared light source which emits infrared light for detection of a height of the examinee's eye.

5. The optometric apparatus according to claim 1 further including
    switching means for switching an examination mode to a near vision examination mode, and
    control means for controlling turning on of the illumination unit according to the switching to the near vision examination mode.

6. The optometric apparatus according to claim 1 further including
    setting means for setting a near vision examination distance, and
    control means for controlling a light quantity of the illumination unit according to the set near vision examination distance.

7. An optometric apparatus for subjectively examining a visual function of an examinee's eye, including:

a pair of right and left lens chamber units, each including a test window and optical elements to be changeably disposed in the test window;

a support unit which supports the lens chamber units so that the units may be converged;

a support rod provided in the support unit;

a near vision examination chart provided movably in an axis direction of the rod;

an illumination unit which illuminates the near vision chart within a movable range of the near vision chart, the illumination unit being provided in each lens chamber unit;

switching means for switching an examination mode to a near vision examination mode; and control means for controlling the illumination unit according to the switching to the near vision examination mode.

8. An optometric apparatus for subjectively examining a visual function of an examinee's eye, including:

a pair of right and left lens chamber units, each including a test window and optical elements to be changeably disposed in the test window;

a support unit which supports the lens chamber units so that the units may be converged;

a support rod provided in the support unit;

a near vision examination chart provided movably in an axis direction of the rod;

an illumination unit which illuminates the near vision chart within a movable range of the near vision chart, the illumination unit being provided in each lens chamber unit;

setting means for setting a near vision examination distance; and control means for controlling the illumination unit according to the set near vision examination distance.

* * * * *